United States Patent [19]

Dines et al.

[11] Patent Number: 4,865,605
[45] Date of Patent: Sep. 12, 1989

[54] MODULAR SHOULDER PROSTHESIS

[76] Inventors: David M. Dines, 333 E. Shore Rd., Manhasset, N.Y. 11030; Russel Warren, Hospital of Special Surgery, New York, N.Y. 10021

[21] Appl. No.: 151,335

[22] Filed: Feb. 2, 1988

[51] Int. Cl.⁴ .............................................. A61F 2/40
[52] U.S. Cl. .................................................... 623/19
[58] Field of Search ...................... 623/16, 18, 19, 20, 623/21, 22, 23

[56] References Cited

U.S. PATENT DOCUMENTS

| | | | |
|---|---|---|---|
| 3,803,641 | 4/1974 | Golyakhousky | 623/19 |
| 3,840,904 | 10/1974 | Tronzo | 623/23 |
| 4,514,865 | 5/1985 | Harris | 623/23 |
| 4,714,471 | 10/1986 | Grundei | 623/20 |
| 4,728,334 | 3/1988 | Spotorno | 623/23 |

FOREIGN PATENT DOCUMENTS

| | | | |
|---|---|---|---|
| 0000549 | 2/1979 | European Pat. Off. | 623/18 |
| 0017743 | 10/1980 | European Pat. Off. | 623/22 |
| 0098224 | 1/1984 | European Pat. Off. | 623/23 |
| 0201407 | 11/1986 | European Pat. Off. | 623/23 |
| 3023354 | 4/1981 | Fed. Rep. of Germany | 623/23 |
| 3329978 | 3/1985 | Fed. Rep. of Germany | 623/23 |
| 2579454 | 10/1986 | France | 623/19 |

OTHER PUBLICATIONS

Zimer, Zimmer Catalog, Warsaw Ind 1978, pp. A1–A7.

Primary Examiner—Richard J. Apley
Assistant Examiner—David J. Isabella

[57] ABSTRACT

A shoulder prosthesis includes a humeral component and a glenoid component. The humeral component comprises an elongated stem, a semispherical head and wherein the head is removably connectable to one end of the stem.

8 Claims, 1 Drawing Sheet

U.S. Patent   Sep. 12, 1989   4,865,605
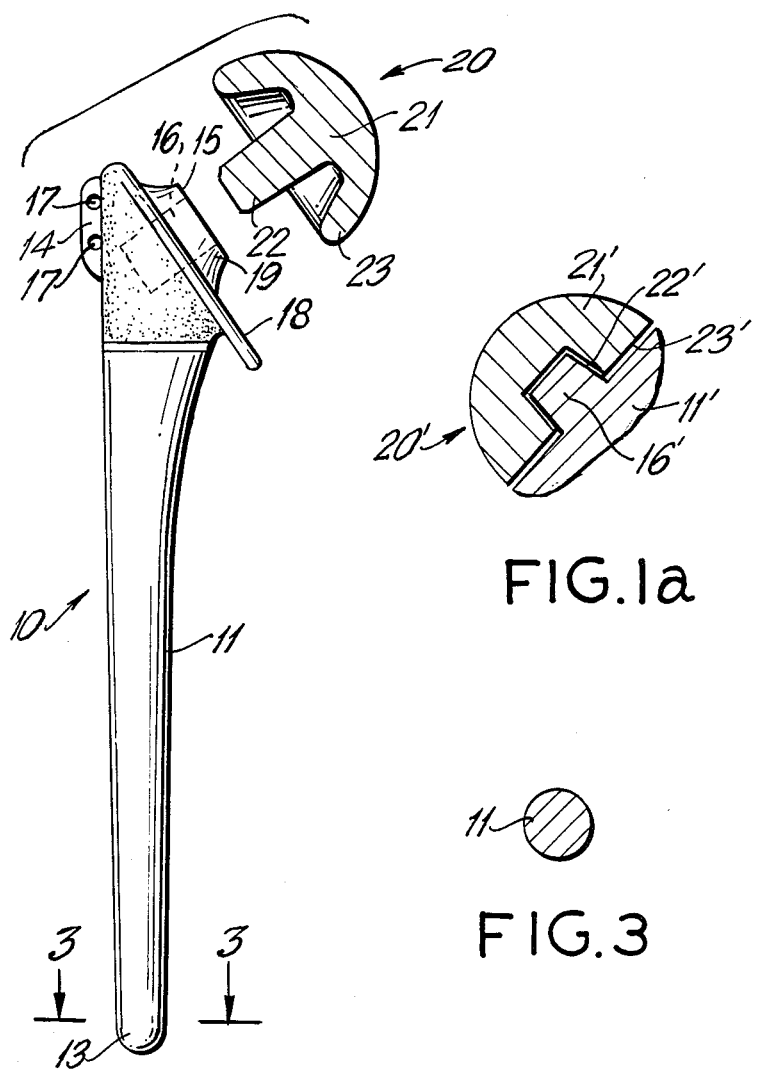
FIG.1a
FIG.1
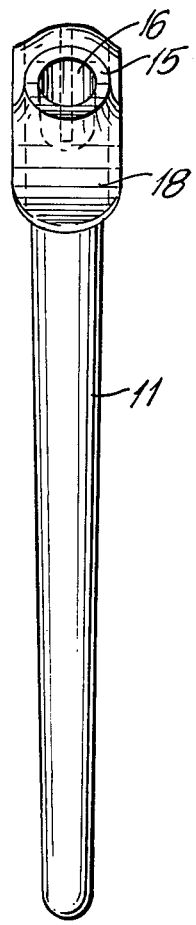
FIG.2
FIG.3
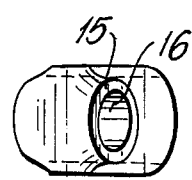
FIG.4
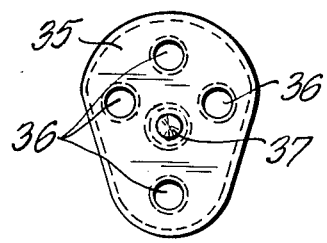
FIG.5
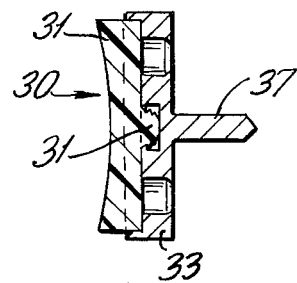
FIG.6

4,865,605

MODULAR SHOULDER PROSTHESIS

BACKGROUND OF THE INVENTION

The present invention relates to a shoulder prosthesis for a total shoulder replacement.

Prostheses for use in a total shoulder replacement are known and essentially consists of a humeral component which is implanted in the proximal humerus and the glenoid component which replaces the socket of the shoulder.

While modularity has been utilized in shoulder prostheses with respect to the glenoid component as can be seen in the McNab-English Total Shoulder Replacement developed by De Puy Incorporated, the question of modularity has not been addressed with regard to the humeral component.

SUMMARY OF THE INVENTION

The main object of the present invention is to provide a modular shoulder prosthesis wherein the humeral component has a modular design which enables different available sized heads to be placed onto a stem which has been implanted in the proximal humerus.

This modular component mechanism allows the surgeon to better set the tensions of the soft tissues about the shoulder during the procedure. This is a definite advantage in total shoulder replacement.

In addition, in those cases of fractures of the proximal humerus in which this implant is used, the modular aspect of the head and stem design affords the surgeon the ability to make revisions to the size of the head if required in the future, without the need for removing the stem implant from the humerus, since at that time the humeral head can simply be removed and the socket or glenoid portion of the shoulder can then be adapted accordingly.

These and other objects and advantages of the present invention are achieved in accordance with the present invention by the modular humeral component of the present invention which has a stem which is seatable into the shaft of the humerus and different available sized heads which are removably connectable to the stem.

This removable connection is preferably carried out by a coupling mechanismm for the head and stem which comprises a Morse taper so that the humeral head can be inserted into the stem via a neck portion which fits into the stem.

In addition to the modular humeral component, the glenoid component can also be made modular as has been disclosed in the prior art with the result that the entire shoulder replacement is modular.

These and other features and advantages of the present invention will be described in connection with the preferred embodiments of the present invention with reference to the attached drawings, wherein:

BRIEF DESCRIPTION OF THE DRAWINGS

FIG. 1 is a side view of the stem and head portions of a humeral component according to the present invention with a Morse taper;

FIG. 1a shows the joining of the head and stem portions in an alternative manner with a Morse taper;

FIG. 2 is a front view of the stem portion of the humeral component according to the present invention;

FIG. 3 is a sectional view along line 3—3 in FIG. 1;

FIG. 4 is a top view of the stem portion of FIG. 1;

FIG. 5 is a top view of the glenoid component; and

FIG. 6 is a sectional view of the glenoid component of FIG. 5 with a plastic insert.

DETAILED DESCRIPTION OF THE INVENTION

Referring now to FIGS. 1-4, the humeral component according to the present invention includes stem 10 having an elongated portion 11 optionally including a rib on both sides thereof which aids in the fixation of the stem in the humerus and stability against rotation. The stem length is preferably in two sizes of 70 mm and 115 mm, and the stem width is in four sizes of 6 mm, 7 mm, 9 mm and 11 mm.

At the distal end of the stem, there is a rounded portion 13 and at the proximal end of the stem is a support surface extending radially from the stem. The support surface having an upper planar surface 18 with a raised collar projecting from plane 18 to plane 19 and having bore 16 extending inwardly from the top plane thereof. The plane 15 is preferably at 45° or 60° to the axis of the stem.

The stem also includes a flange portion 14 including fixation holes 17 which aid in the fixation of the implant after embedded in the humerus.

The entire stem portion is preferably coated with a porous material for aiding in the fixation.

The head 20 shown in FIG. 1 includes a spherical sectional body 21 having a bottom flange 23 which abuts plane 18 and a stem 22 for inserting into bore 16 in a tightly fitting manner. Both the bore 16 and neck 22 are tapered in a Morse taper and provide a friction fit when placed in a connected condition.

The head 21 has a diameter in one of four sizes including 28 mm, 40 mm, 44 mm and 48 mm and the height of the head is preferably 15 mm to 27 mm.

In FIG. 1a, a modified embodiment of the present invention is shown wherein head body 21' includes bore 2' and stem 11' includes a stem 16' at the top thereof. As can be seen in FIG. 1a, bore 22' and stem 16' have a Morse taper which provide a friction fit when the two are connected together.

FIGS. 5 and 6 show the glenoid component 30 in more detail including semi-spherical plastic seating surface 31 for engaging head 20 and stem portion 32 a "christmas tree" which is cut and is inserted into base 33 which has a stem 37 for inserting into bore and screw holes 36 for fixation.

The base of the glenoid component is preferably metal on plastic with a porous coating and the stem 32.

It will be appreciated that the instant specification and claims are set forth by way of illustration and not limitation, and that various modifications and changes may be made without departing from the spirit and scope of the present invention.

What is claimed is:

1. A humeral component for a shoulder prosthesis, comprising:
   an elongated stem having one a distal portion for insertion into a humerus and a proximal end portion having support surface extending radially from said stem; for abutting against the humerus, the surface having a planar upper surface with a raised collar formed thereon, said collar having a tapered aperture formed therein and extending downwardly through said collar and into said proximal end portion;

a head having means forming a semispherical outer surface an a concave recessed inner surface, said inner surface having a tapered pin extending from a bottom portion of said recess and outwardly thereof and dimensioned so as to form a clearance therearound with said inner surface of the shell, wherein the recess is configured to receive and surround the raised collar when said tapered pin is tightly received in said aperture thereby securing said joint head to the stem; and, wherein the recess is configured to receive the projecting surface and wherein the pin has a taper configured to be tightly received in the aperture to form a friction fit with the semispherical outer surface surrounding the projecting surface.

2. The shoulder prosthesis according to claim 1, wherein the stem tapers in cross section from the proximal end toward the distal end and has radially projecting fins along the length thereof.

3. The shoulder prosthesis according to claim 1, wherein the distal end portion of the stem is rounded.

4. The shoulder prosthesis according to claim 1, wherein the stem is covered with a porous coating.

5. The shoulder prosthesis according to claim 1, wherein the stem has a flange in the vicinity of said proximal end portion thereof with fixation holes therein.

6. The shoulder prosthesis according to claim 1, wherein the stem has a length in the range of 70 to 115 mm and a width of from 6 to 11 mm.

7. The shoulder prosthesis according to claim 1, wherein the head has a diameter from 28 to 48 mm and a thickness of 15 to 27 mm.

8. The shoulder prosthesis according to claim 1, wherein the stem defines a longitudinal an axis and the planar surface extends from 45° to 60° to the axis of the stem.

* * * * *